United States Patent [19]

Morantte, Jr.

[11] Patent Number: 4,587,972
[45] Date of Patent: May 13, 1986

[54] DEVICE FOR DIAGNOSTIC AND THERAPEUTIC INTRAVASCULAR INTERVENTION

[76] Inventor: Bernardo D. Morantte, Jr., 6713 Woodhaven Pl., Riverbank, Calif. 95367

[21] Appl. No.: 631,381

[22] Filed: Jul. 16, 1984

[51] Int. Cl.[4] .................... A61B 8/12; A61B 17/36
[52] U.S. Cl. .................................. 128/660; 128/4; 128/303.1; 128/692
[58] Field of Search .............. 128/4, 6, 660, 661, 128/662, 663, 303.1, 692

[56] References Cited

U.S. PATENT DOCUMENTS

| 3,352,303 | 11/1967 | Delaney. | |
|---|---|---|---|
| 3,467,098 | 9/1969 | Ayres. | |
| 3,577,981 | 5/1971 | Kuris. | |
| 3,938,502 | 2/1976 | Bom. | |
| 4,072,147 | 2/1978 | Hett. | |
| 4,120,293 | 10/1978 | Muckerheide. | |
| 4,146,019 | 3/1979 | Bass et al. | 128/6 |
| 4,207,874 | 6/1980 | Choy. | |
| 4,266,548 | 5/1981 | Davi | 128/303.1 |
| 4,266,549 | 5/1981 | Kimura. | |
| 4,375,818 | 3/1983 | Suwaki et al. | 128/4 X |
| 4,462,408 | 7/1984 | Silverstein et al. | 128/4 X |

OTHER PUBLICATIONS

*Ultrasonic Diagnostic Instruments,* Science Magazine, vol. 210, by Popp and Macovski, 17 Oct. 1980.

*Primary Examiner*—William H. Grieb
*Attorney, Agent, or Firm*—Worrel & Worrel

[57] ABSTRACT

A device for imaging and removing obstructions from blood vessels and the like having a flexible tubular housing dimensioned for insertion within a blood vessel; a fiberoptic bundle adapted to conduct laser beams to an obstruction for the destruction of portions thereof; and an ultrasound portion adapted to generate ultrasonic waves processable to create an image of an obstruction.

24 Claims, 10 Drawing Figures

DEVICE FOR DIAGNOSTIC AND THERAPEUTIC INTRAVASCULAR INTERVENTION

BACKGROUND OF THE INVENTION

1. Field of the Invention

The present invention generally relates to a device for diagnosing and removing obstructions within the lumens of hollow, substantially tubular structures and more particularly to such a device adapted for use in diagnosing and removing obstructions in blood vessels.

2. Description of the Prior Art

The debilitating effects of obstructions to the flow of blood in the cardiovascular system of humans and animals have long been recognized. Such obstructions can take many forms and arise in many different manners. For instance, accretion of inorganic and organic materials on the walls of blood vessels have long been known as a cause of an overall reduction in the cross-sectional area of the lumen of the vessel with a consequent diminishing effect on the rate of blood flow therethrough. Further, a number of pathologies have been identified as the cause of intravascular occlusions and partial obstructions, such as atheromas and the like.

While some such obstructions respond favorably to medicinal or chemical treatment, either to effect a dilation of the vessel or a chemically induced erosion or to induce the breaking up or dissolution of the material obstructing the blood vessel, it has long been known that such chemical applications have limited utility and are restricted to use in a rather insubstantial portion of pathological environments, particularly those involving tissue growth across the lumen or bore of a blood vessel.

Various apparatuses have been proposed which are adapted for use in physically intervening within the vascular cavity to remove the obstruction. For example, it has been proposed to employ laser generating or similar apparatuses to cause a disintegration of the obstruction of the blood vessel. While some such apparatuses are useful for their intended purposes, it has long been known that associated devices and methods for permitting the visualization of the pathological tissue during and prior to the attempted removal thereof have been largely deficient and unsatisfactory in one or more respects, such as the inability accurately to gauge the dimensions of the obstruction before and during the performance of the removal technique for which the therapeutic apparatus is intended to be used. The use of the various visualization methods and devices heretofore proposed often necessitates the interruption of blood flow through the vessel being treated, or require interruption of the treatment period for substantial periods of time, in order that the remaining portions of the obstruction can be visualized. Thus, it has been known that conventional visualization techniques and devices used in conjunction with known therapeutic tools and apparatuses for the removal of obstructions often do not permit accurate determinations of obstruction dimensions during treatment for precise imaging of the progressive reduction of the obstruction during the treatment, whereby the treatment can be minimized substantially to that necessary without exceeding safe levels of treatment.

Therefore, it has long been known that it would be desirable to have an improved device for visualizing obstructions in the lumens of cardiovascular vessels and the like and for removing such obstructions. Further, it has long been known that it would be desirable to have such a device which can be constructed in a variety of dimensions for use in removing pathological growths, inorganic accumulations, and other obstructions to free blood flow in blood vessels of varying sizes with a precision of imagery and therapeutic application heretofore unattainable.

OBJECTS AND SUMMARY OF THE INVENTION

It is therefore an object of the present invention to provide an improved device for intervening in substantially tubular structures and more particularly in blood vessels for the removal of obstructions therefrom.

Another object is to provide such a device which is adapted for use in visualizing the dimensions and contours of obstructions in blood vessels before, during and after the removal thereof.

Another object is to provide such a device which is adapted to be selectively operated to image obstructions in blood vessels and to remove or destroy such obstructions.

Another object is to provide such a device which permits the visualization of the configuration and dimensions of obstructions in blood vessels simultaneously with the destruction of such obstructions.

Another object is to provide such a device which is adapted to be used in visualizing and removing obstructions from blood vessels with minimal or no interruption of blood flow therethrough.

Another object is to provide such a device which is adapted to be dimensioned and constructed in a wide variety of sizes and flexibilities for insertion in blood vessels of differing sizes.

Another object is to provide such a device which is adapted to be constructed inexpensively to permit the economical disposal of the device after use thereof to prevent the possible transmission of diseases from one therapeutic subject to another.

Further objects and advantages are to provide improved elements and arrangements thereof in an apparatus for the purposes described which is dependable, economical, durable and fully effective in accomplishing its intended purposes.

DESCRIPTION OF THE PREFERRED EMBODIMENT

Figures 1, 2:
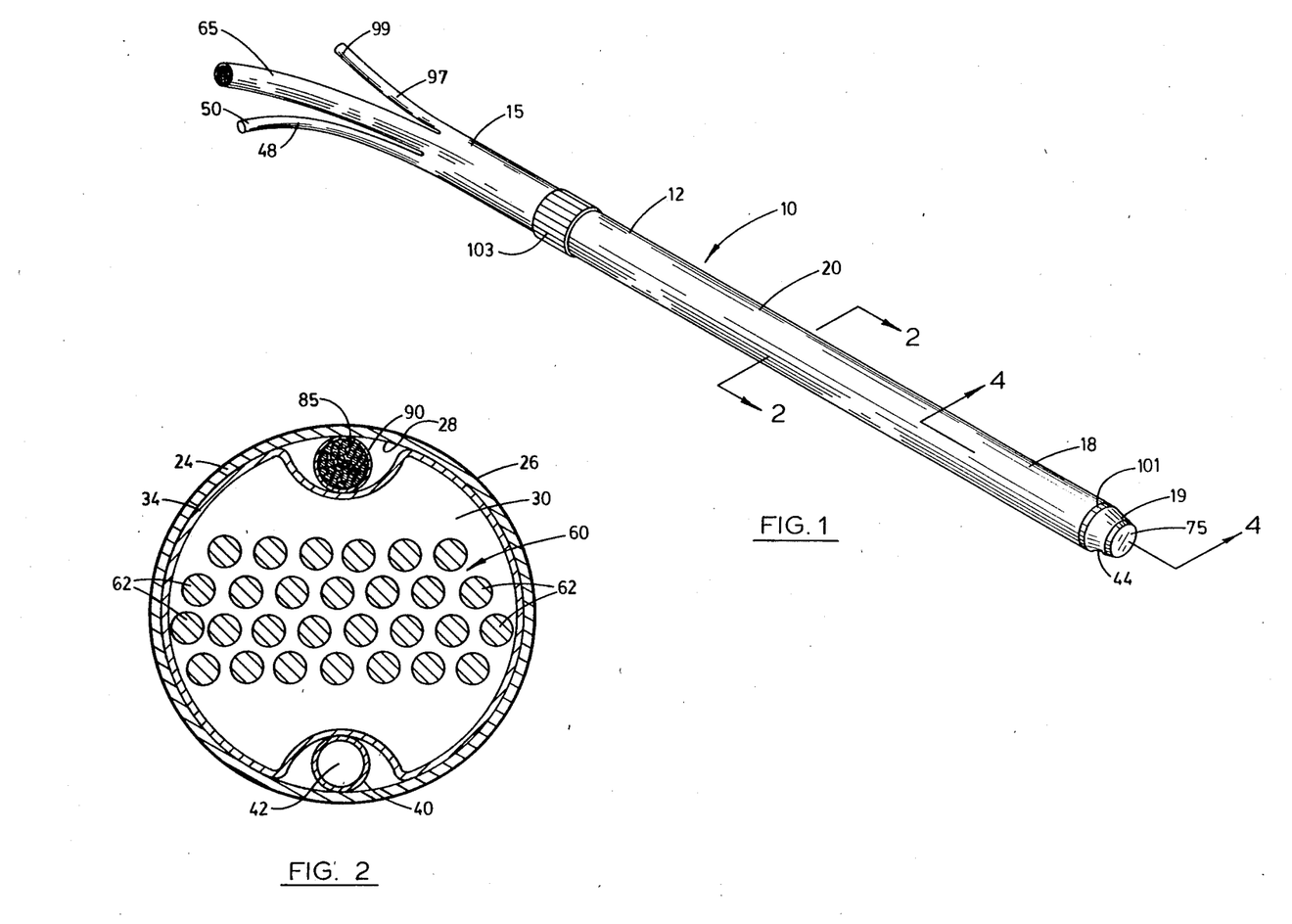
FIG. 1 is a perspective view of a first form of the device of the present invention.
FIG. 2 is an enlarged transverse section taken on line 2—2 in FIG. 1.
Figures 3, 5:
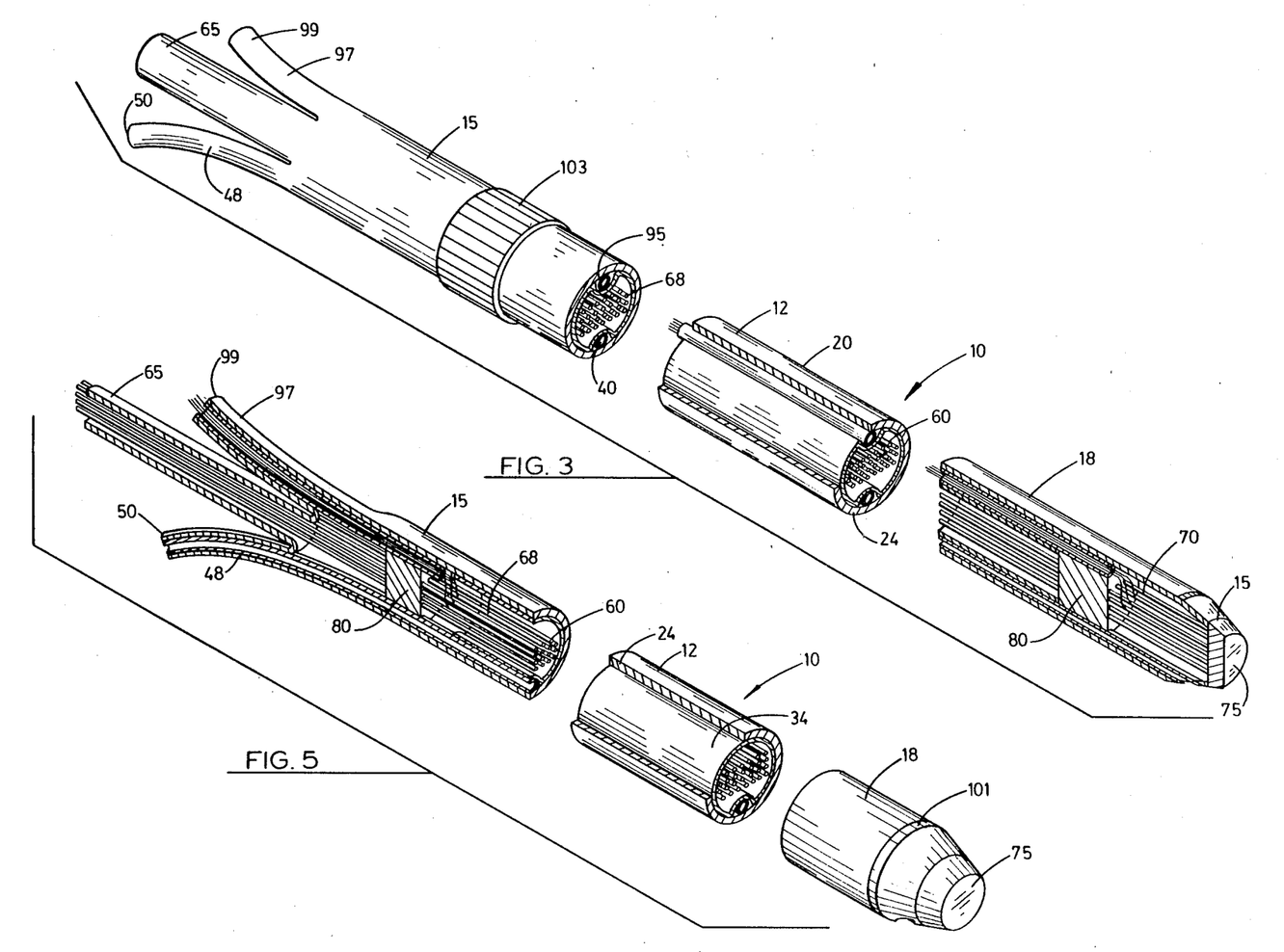
FIG. 3 is a somewhat enlarged, fragmentary view of the device of FIG. 1 with portions removed to illustrate the arrangement of portions internally thereof.
FIG. 5 is a somewhat enlarged, fragmentary perspective view of a second form of the device of the present invention.

Referring more particularly to the drawings, the device embodying the principles of the present invention is designated generally by the numeral 10 in FIGS. 1 and 3. As shown therein, the device 10 generally provides a catheter or housing 12 having a first or proximal end portion 15; an opposite, second or distal end portion 18 having an endmost edge or tip 19; and an elongated, intermediate portion 20 extending between the distal end portion and proximal end portion. As shown in FIG. 3, portions of the distal end portion 18 and the intermediate portion 20 have been removed for purposes of illustration. While the device finds application in a wide variety of operative environments, it has particular utility for intravascular intervention and, accordingly, reference is made herein to such use of the device, although it is understood that neither the device nor its operation are to be limited to such environments.

The housing 12 provides a wall 24 having an exterior surface 26 and an interior surface 28. Preferably, the wall 24 is constructed of a substantially flexible, electrically-insulating material. As can best be seen in FIG. 2, the wall 24 preferably has a substantially circular, cross-sectional configuration of predetermined diameter whereby the distal end portion 18 and intermediate portion 20 of the housing 12 have predetermined dimensions. If necessary for use in a particular operative environment, the distal end portion and intermediate portion can be tapered distally to provide a progressively lesser outside diameter from the proximal end portion to the distal end portion. It will be recognized that the diameters of the portions of the wall 24 will largely depend upon the particular application for which the device is intended to be used. For instance, it will be understood that if the device 10 is to be used for removing obstructions in a large artery, the diameter of the wall 24 can be greater than that of the wall of a device 10 intended for use in a smaller branch artery or vein.

The housing 12 can also be constructed having virtually any desired length for use in various particular biological environments. Thus, it will be recognized that the diameter of the wall 24 of the housing 12 of the device 10 illustrated in FIG. 1, in relation to the length of the housing as determined by the separation between the proximal end portion 15 and the distal end portion 18, is a result of illustrative restrictions and it is understood that the length of the housing 12 in relation to the diameter of the wall 24, will, in many constructed embodiments of the present invention, be substantially greater than that illustrated.

The interior surface 28 of the wall 24 bounds a passage or chamber 30 extending substantially completely from the proximal end portion 15 to the distal end portion 18.

A sleeve 34 is disposed within the chamber 30 and extends from the proximal end portion 15 incompletely to the distal end portion 18. The sleeve is dimensioned closely to conform to the interior surface of the wall 24 incompletely circumferentially thereabout. The sleeve is preferably constructed of electrically-insulating, substantially flexible material.

As can best be seen by reference to FIGS. 1, 2 and 3, the housing 12 provides an elongated, substantially cylindrical conduit or tube 40 extending incompletely longitudinally the length of the housing and contained in the chamber 30 between the interior surface 28 of the wall 24 and the sleeve 34. Preferably, the tube 40 is constructed of any suitable substantially flexible material. The tube can be constructed separately from the materials comprising the wall 24 or, alternatively, can be formed unitarily with the wall at the time of fabrication thereof. The tube 40 provides an internal passage 42 extending longitudinally therethrough. The housing 12 provides a port or aperture 44 in the distal end portion 18 thereof communicating through the wall 24 with the passage 42 of the tube 40. The housing 12 further provides a tubular connection member 48 extending from the proximal end portion 15 having a terminous or end 50. The tubular connection member is disposed in fluid-flow relation to the tube 40 and the passage 42 thereof. Preferably, the tubular connection member is constructed of substantially flexible material and is dimensioned for the insertion of guide wires and the like therein, and, further, is of sufficient dimensions to permit the flow of blood and other fluids therethrough. The end 50 of the tubular connection member 48 is preferably constructed to permit connection thereof to devices or apparatuses suitable for the measurement of the hemodynamic characteristics of a vascular system into which the device 10 is inserted. Further, a guide wire or the like can be inserted through the end 50 and the tubular connection 48 for introduction into the passage 42 of the tube 40, if desired, to assist the manipulation of the device 10 within a tubular structure, such as a blood vessel or the like.

Figure 4:
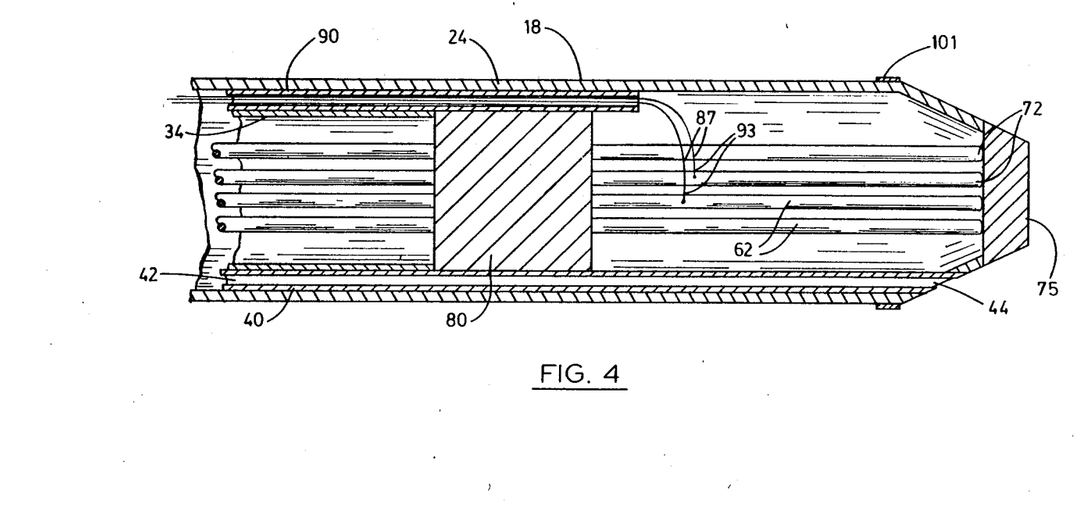
FIG. 4 is a somewhat enlarged longitudinal section taken on line 4—4 in FIG. 1.

As can best be seen in FIGS. 2, 3 and 4, the chamber 30 of the housing 12 contains a fiberoptic bundle 60 comprising a plurality of elongated, fiberoptic fibers 62 disposed in substantially axially parallel relation and extending longitudinally within the chamber from the proximal end portion 15 to the distal end portion 18. The fibers 62 can be constructed of any suitable conductive material adapted to conduct light from a light source axially through the fiber and, preferably, the fibers are constructed of such material which is particularly adapted to conduct light from a laser-generating source axially therethrough and to emit such light from the tip 19. Preferably, although not necessarily, the fibers are round in cross-sectional configuration, as shown in FIG. 2, although other forms, such as "strip"-type fibers can be used. As can best be seen in FIGS. 1 and 3, the proximal end portion 15 of the housing 12 provides a fiberoptic connector portion 65 extending longitudinally therefrom and having a substantially tubular construction continuous with the housing 12 and the chamber 30 thereof. The fiberoptic bundle has a proximal end portion 68 disposed within the proximal end portion 15 of the housing 12 and the fiberoptic connector portion 65, and a distal end portion 70 remote therefrom and disposed within the distal end portion 18 of the housing 12. Each fiber 62 provides a distal terminus 72, as can best be seen in FIG. 4. As will be described hereinafter, the selective application of light from a laser source to one or more of the fibers 62 at the proximal end portion 68 of the fiberoptic bundle 60 will generate a beam of a predetermined energy level which will be discharged substantially axially of the terminus 72 of each fiber 62 to which such laser light is applied. Preferably, although not necessarily, the proximal end portion 68 of the fiberoptic bundle and the fiberoptic connector portion 65 are adapted to be connected to an appropriate laser source which is capable of either simultaneously or sequentially generating laser energy through one or more fibers 62 to permit the discharge of a predetermined amount of laser light or energy from the termini of such fibers for impingement of such laser energy upon a target object of known size, such as an obstruction within a blood vessel, for the precise destruction thereof.

As can best be seen in FIGS. 1, 2, 3 and 4, the housing 12 mounts an end cap or acousto-optic lens 75 on the distal end portion 18 thereof. The acousto-optic lens is disposed to permit the passage of laser beams emitted from the termini 72 of the fibers 62 therethrough and operates to focus the beams at a predetermined focal point distally external of the housing a predetermined distance. Preferably, the focused beam will have predetermined transverse dimensions depending upon the number and spacing of the optic fibers utilized to transmit the beam. Preferably, the lens 75 is constructed of a material suitable to permit both laser beams and ultrasonic waves to pass therethrough. Optionally, if an acousto-optic lens is not used, the termini 72 of the fibers 62 can be arranged or shaped in a suitable manner or configuration to permit efficient focusing of the laser beam in order to maximize the efficiency and precise application of the beam in an operative environment. Focusing and steering can also be achieved, or further optimized, by utilizing the equipment used to generate the laser beams in a "phase array" manner.

As is discussed more fully below, the fibers 62 in the distal end portion 70 of the fiberoptic bundle 60 are preferably spaced a predetermined distance from adjacent fibers. It is understood that arrangement of the fibers shown in FIG. 2 is illustrative only and can be varied substantially within the scope of the present invention, although it will be appreciated that the spacing of the fibers is critical if steering of the laser beams is desired.

Upon reference to FIGS. 3 and 4, it will be seen that the housing 12 provides a block of sound-absorbing material or lossy backing 80 within the chamber 30 in the distal end portion 18 thereof. The lossy backing should have an acoustic impedance substantially similar to that of the piezoelectric material described hereafter effectively to dissipate the ultrasonic waves and to prevent the production of an image of the lossy backing 80 when the waves echoed therefrom inpinge upon the piezoelectric material. The optical fibers 62 are extended through the lossy backing and are individually substantially completely circumscribed by the portions thereof. Preferably, the lossy backing is constructed of a sound-absorbent material to permit the travel of ultrasonic waves toward the distal end portion 18 within the chamber 30, as is described in greater detail below, and to reduce the travel of waves toward the proximal end portion 15. The lossy backing further serves the purpose of dissipating any ultrasonic waves generated which travel toward the proximal end portion, thus reducing interference. The lossy backing also provides a dampening effect on the excited piezoelectric material to prevent continued generation of waves thereby which might otherwise create artifacts. Such dampening is essential in order to permit the piezoelectric material to attain a ready state for the reception of echoed ultrasonic waves. Preferably, the lossy backing 80 is dimensioned substantially completely to occlude the chamber 30 at its point of deployment. Alternatively, or additionally, each fiber 62 can be coated with a sound-absorbing material along its length from the proximal end portion 68 incompletely longitudinally toward the distal end portion 70, leaving a portion of the distal end portion uncoated.

A selected number of fibers 62 of the fiberoptic bundle 60 are coated substantially completely from the lossy backing 80 to the terminus 72 thereof with a suitable material having high piezoelectric properties whereby, upon the application of electrical energy thereto, ultrasonic waves of a predetermined range of wavelengths will be generated by activation or excitation of the piezoelectric material and whereby, upon impingement of ultrasonic waves or energy upon the piezoelectric material, electrical impulses will be generated. For instance, polyvinylidine difluoride is exemplary of the materials from which the piezoelectric material can be selected. Of course, any other suitable material having high piezoelectric properties can be employed for this purpose. Further, preferably the coated fibers are spaced from each other a distance equal to or less than one half the anticipated wavelength of the ultrasonic waves generated by the excitation thereof, whereby artifacts in the resultant ultrasonic image are minimized. An alternative to coating the fibers would be the use of optic fibers constructed of material having high piezoelectric properties. Optionally, the fibers can be coated substantially over their entire lengths with the material.

As can best be seen in FIGS. 2, 3, and 4, the housing 12 further provides an electrode bundle 85 having a plurality of electrical conductors or electrodes 87 extending longitudinally within the chamber 30 from the proximal end portion 15 toward the distal end portion 18. The electrodes 87 are elongated, electrically-conductive strands disposed in close proximity to each other within an electrically-insulating sheath 90 disposed intermediate the sleeve 34 and interior surface 28 of the wall 24 substantially diametrically opposite the tube 40. Preferably, each electrode 87 is individually electrically insulated from adjacent electrodes. Each electrode provides a distal end portion 93 connected on the piezoelectric coating of an individual fiber 62 intermediate the lossy backing 80 and the terminus 72 of the fiber, whereby application of electrical energy to the electrode will conduct an electrical charge to the piezoelectric material. The electrically-stimulated piezoelectric material then emits ultrasonic waves which travel axially of the housing, preferably providing a scanning angle in the range of from about 30 to 45 degrees. Each electrode 87 further provides a proximal end portion extended from the proximal end portion 15 of the housing 12 bundled with the proximal end portions of the other electrodes 87 within an electrode connection member 97 of substantially tubular configuration, constructed preferably of an electrically-insulating material. The electrode connection member 97 provides a terminus 99 adapted to be connected to means for generating electrical impulses and for receiving electrical impulses conducted through the proximal end portions of the electrodes 87 for analysis thereof, as is described in greater detail below.

The distal end portion 18 of the housing 12 mounts an annular marker element 101 of metal or other suitable construction capable of visualization by fluoroscopy or similar means whereby the approximate location of the distal end portion within a blood vessel can be determined during the operation of the device 10.

The proximal end portion 15 of the housing 12 mounts a substantially cylindrical protective ring 103 disposed in circumferentially close-fitting relation thereon. Preferably, the ring 103 is of rigid metal or plastic construction to permit manual manipulation thereof during the operation of the device 10 and to prevent damage to the housing 12, fiberoptic bundle 60, or electrode bundle 85 by compression or squeezing thereof.

An alternative construction of the device 10 of the present invention is illustrated in FIG. 5 in a fragmentary, partially cut-away view. The alternative form of the device illustrated therein is substantially identical in all respects to the device 10 illustrated in FIGS. 1, 2, 3 and 4, excepting that the lossy backing 80 is disposed in the proximal end portion 15 of the housing in close circumscribing relation to the fibers 62 on the proximal end portions 68 thereof. Thus, a greater length of each fiber 62 having piezoelectric material coated thereon is coated with such material. The device 10 shown in FIG. 5 is adapted to be constructed having a gradually tapering outside diameter with a minimum diameter at the distal end portion 18 for use in smaller blood vessels. Preferably, the inner surface of the sleeve 34 is coated with an appropriate sound-absorbent material to minimize any possible "ringing" effect.

Figure 6:
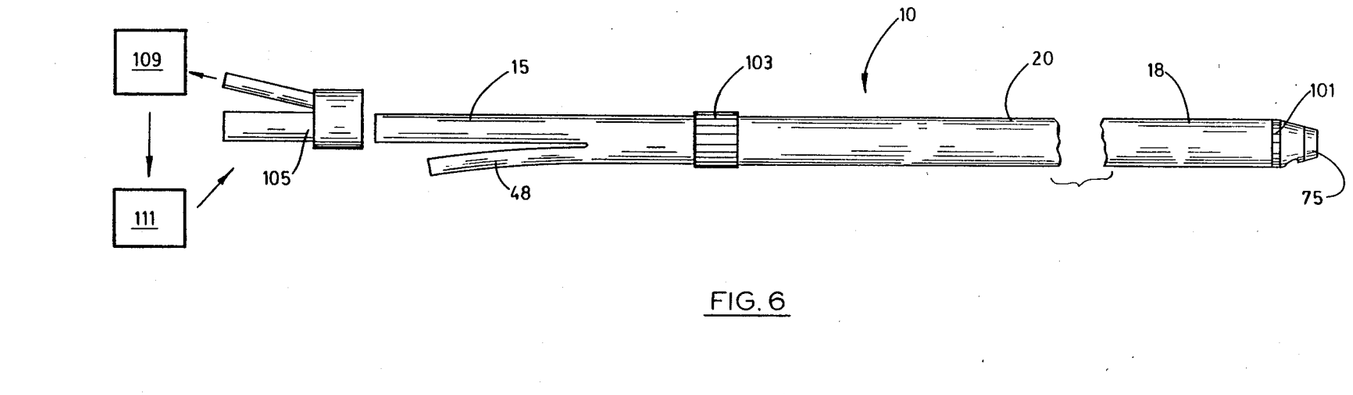
FIG. 6 is a fragmentary side elevation of a third form of the device of the present invention shown schematically linked to sources of ultrasonic and laser energy.

A second alternative construction of the device 10 of the present invention is illustrated in FIG. 6 and is similarly adapted for operative deployment in small vessels. As shown therein, the fiberoptic connector portion 65 and the electrode connection member 97 are detached from the housing 12 and are incorporated in an acousto-optic coupling member 105. The acousto-optic coupling member houses a transducer element comprising a plurality of electrodes and a region of piezoelectric material adapted to be excited by the application of electrical energy thereto by the electrodes. The acousto-optic coupling member is adapted to be connected on the proximal end portion 15 of the housing 12 to serve as a link between a source of electrical energy 109 and the transducer element therein, and between a source of laser energy 112 and the fibers 62 of the fiberoptic bundle 60. When so connected, excitation of the piezoelectric material in the acousto-optic coupling member will generate ultrasonic waves directed axially within the housing.

Figure 7:
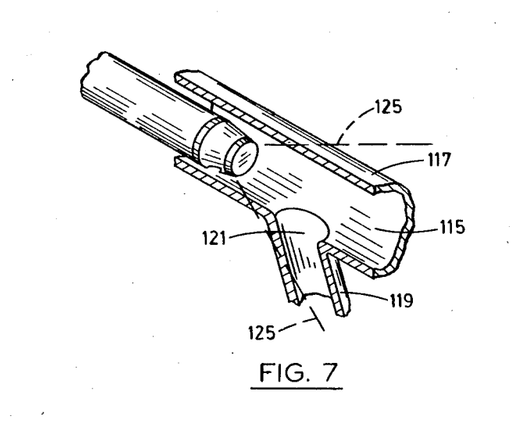
FIG. 7 is a perspective view of a portion of the device of FIG. 1 shown deployed in a typical operative environment with the distal end portion thereof disposed within the lumen of a blood vessel.
Figure 9:
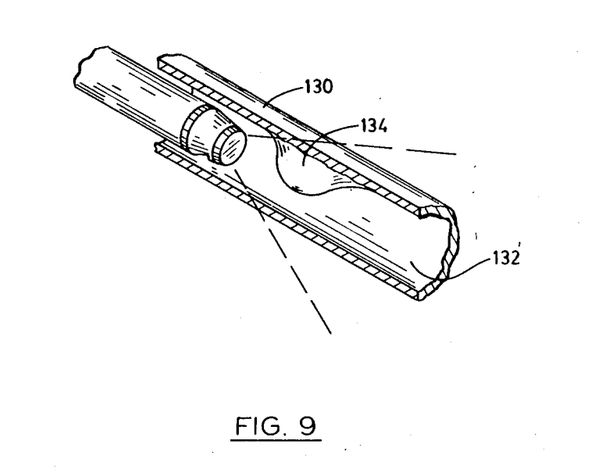
FIG. 9 is a perspective, fragmentary view of the device of FIG. 1 shown deployed in a typical operative environment with the end portion thereof disposed in proximity to an obstruction within the lumen of a blood vessel.

The forms of the device 10 of the present invention illustrated in FIGS. 1 through 6 are each adapted for operation in similar operative environments, such as those illustrated in FIGS. 7 and 9. As shown in FIG. 7, the distal end portion 18 is inserted within the lumen 115 of a blood vessel 117 having a branched vessel 119 intersecting therewith, the branched vessel having a lumen 121 communicating with the lumen 115. The range of transmission of ultrasonic waves from the device 10 is illustrated in FIG. 7 in dashed lines 125.

In FIG. 9, the device 10 is shown deployed in a typical operative environment in a blood vessel 130, such as an artery or the like having a lumen 132 partially occluded by an obstruction 134 attached to or protruding from the vessel 130 transversely into the lumen 132.

Figure 8:
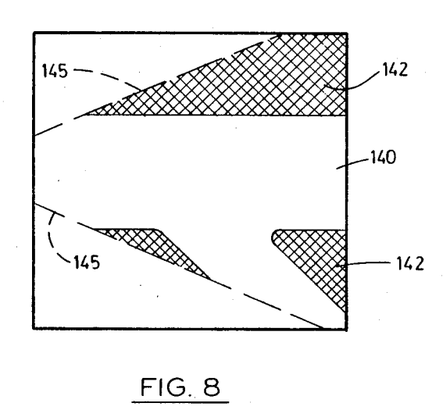
FIG. 8 is a schematic depiction of an ultrasound generated image obtained by the operation of the device of FIG. 1 deployed in an attitude illustrated in FIG. 7.

FIG. 8 is a substantially schematic illustration of an ultrasonic image 140 generated by the operation of the device 10 in the typical operative environment illustrated in FIG. 7. The checked or cross-hatched portions 142 represent substantially solid matter, such as the vessel 117 and surrounding tissues. The dashed lines 145 illustrate the boundaries of the image generated. The ultrasonic image 140, illustrated in FIG. 8, indicates a lack of obstructions within the vessel 117.

Figure 10:
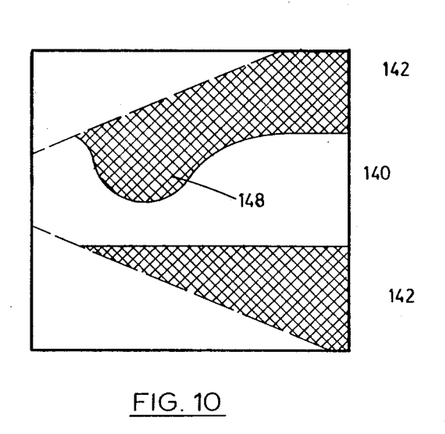
FIG. 10 is a schematic depiction of an ultrasonically generated image of the blood vessel and the obstruction therein obtained by the operation of the device of FIG. 1 in the operative attitude illustrated in FIG. 9.

In FIG. 10, an ultrasonic image 140 is schematically depicted to represent the image generated by the operation of the device 10 in the operative environment illustrated in FIG. 9. The checked or cross-hatched portion 142 again represents substantially solid material with the remainder of the image bounded by the dashed lines 145 indicating unobstructed, substantially non-solid material or areas. The obstruction 134 is depicted as a lobed image 148.

OPERATION

The operation of the described embodiment of the subject invention is believed apparent and is briefly summarized at this point. Although the device 10 of the present invention is useful in a wide variety of operative environments, it finds particular utility in the removal of obstructions in blood vessels and the like and, therefore, the description of the operation of the device herein is made with particular reference to such application.

In preparing the device 10 for the imaging and removal of an obstruction from a blood vessel, such as is illustrated in FIG. 9, the device must first be connected to a source or sources of laser energy and electrical energy. Preferably, the source of electrical energy utilized is incorporated within an apparatus (not shown) having the capability of generating electrical impulses and converting and analyzing electrical impulses received thereby to produce an image, such as that schematically depicted in FIG. 10. Preferably, such a source of electrical energy, or analysis unit, is adapted to be connected in electrically-conductive relationship to the electrodes 87 to energize a selected number of such electrodes for exciting the piezoelectric material on a desired number of fibers 62 and further to apply electrical impulses to such fibers in a variety of manners, such as by a "phase array" method or simultaneously, as required by the particular operative environment. It is preferable that the electrical source be adapted to be applied to the electrodes to activate the piezoelectric material to cause the material to emit ultrasound having a frequency in the range of from about 5 MHz to 10 MHz. A lower frequency will not permit optimum resolution, and a higher frequency might result in undesirable or excessive heat generation in tissues impacted by the ultrasonic waves. Additionally, the analysis unit should be capable of interpreting electrical impulses generated by the piezoelectric material upon contact of the material by ultrasonic waves echoed from solid structures within the vessel lumen and transmitted to the analysis unit by the electrodes, in any well known manner utilizing conventional analysis apparati, or utilizing processing equipment designed especially for use with the device of the present invention.

The fiberoptic bundle 60 must also be connected to a source of laser energy adapted to conduct laser beams individually into and axially through the fibers 62. For this purpose, a laser source should be selected having the capacity to be connected to the fiberoptic connector portion 65 selectively and individually to transmit a laser beam through the fiberoptic connector portion and into a selected number of fibers. The fibers can be activated individually or simultaneously in a group of a selected number of such fibers. Further, the fibers can be activated sequentially, if so desired. Of course, the ability to pump the laser and, hence, the fibers sequentially would depend on the efficiency of the laser source. Preferably, the laser source has a variable power output capacity to each unit for adjustment thereof to meet the desired penetration based on the dimensions of the obstruction encountered and to minimize thermal injury of the walls of the blood vessel or the like into which the device 10 is inserted.

If it is desired that hemodynamic measurements be made during the operation of the device 10, the tubular connection 48 on the proximal end portion 15 of the housing 12 can be connected to a conventional apparatus adapted for such purpose, whereby upon insertion of the distal end portion 18 of the housing 12 into, for instance, an artery or the like, the flow of blood within the artery will carry blood into the aperture 44 on the distal end portion 18 to conduct the blood through the passage 42 of the conduit 40 to permit hemodynamic quantification. While hemodynamic measurements will normally be desired to be taken during the performance of procedures for which the device is adapted, if hemodynamic measurements are not necessary in the procedure performed employing the device 10, the tubular connection 48 can be sealed to prevent the exit of blood therefrom or an appropriate guide wire structure can be inserted therethrough and passed through the passage 42 to the vicinity of the aperture 44 to permit use of the guide wire in manipulating the housing 12 to orient the fiberoptic bundle 60 in a desired attitude relative to the blood vessel or the like into which it has been inserted.

Upon connection of the fiberoptic connector portion 65 and the electrode connection member 97 to their appropriate energy sources, the device 10 can be utilized in the manner described hereinafter.

In the operation of the device 10 for the purposes of removing obstructions from blood vessels, appropriate sterile techniques will be employed in preparing the entry site for insertion of the distal end portion 18 of the housing 12 into the vessel to be treated, or into a vessel connecting therewith. Preferably, the entry site will be remote from the operative site of the obstruction a distance less than the length of the housing 12. An appropriate puncture is made into a suitable blood vessel for insertion of the distal end portion 18, and the lumen of the vessel is exposed to provide an aperture through which the distal end portion can be introduced. In certain operative environments, such as for the removal of obstructions in cardiac blood vessels, it may prove necessary to utilize a guide catheter to dispose the device in proximity to the operative site.

The housing ring 103 on the proximal end portion 15 of the housing is grasped manually and the housing 12 is slid forwardly to advance the distal end portion 18 toward the obstruction 134 within the lumen 132 of the vessel 130, substantially as illustrated in FIG. 9. Preferably, the approximate distance from the entry site to the obstruction is roughly calculated in advance of performance of the technique using conventional contrast or radio opaque dye studies. During the passage of the distal end portion 18 within the vessel 130, it is desirable that fluoroscopic or similar techniques be employed to observe the progress of the portion of the housing bearing the annular marker 101 in order best to determine when the operative site has been neared.

Upon deployment of the distal end portion 18 in close proximity to the anticipated location of the obstruction 134, the ultrasound source is activated to transmit electrical energy through the electrodes 87 into the piezoelectric material coated on the fibers 62 to generate ultrasonic vibrations therefrom. Preferably, as discussed previously, the electrodes are energized in a phase array manner to provide an angle of ultrasound wave travel of about 30 to 45 degrees. Echoed waves returning to the piezoelectric material after contacting the obstruction 134 and vessel 130 will deform the material to generate signals through the electrodes which are received by the ultrasound apparatus provided to process the signals and reconstruct an image of the lumen and walls of the vessel as well as of the obstruction, substantially as depicted schematically in FIG. 10, whereby the relative distance from the distal end portion 18 of the obstruction, as well as its dimensions, can be gauged. The housing is then manipulated to dispose the distal end portion 18 a selected distance from the obstruction 134 and the laser source is then activated to transmit laser beams axially through a selected number of the fibers 62. The duration of transmission of the laser beam and the number of fibers activated among those in the fiberoptic bundle 60 will be largely dependent upon the configuration and size of the obstruction. Upon completion of the generation of the laser beams, an ultrasound image is once again generated to determine the amount of the obstruction, if any, remaining. The remaining portions of the obstruction are then impinged by laser beams generated by the laser source through the fibers and subsequently another ultrasound image is generated, once again to determine whether any portion of the obstruction remains. These procedures are repeated until a satisfactory reopening of the lumen 132 of the vessel has been obtained. Once reopening of the lumen is accomplished, hemodynamic measurements can be taken through the aperture 44 and tube 40 to confirm the efficacy of such reopening of the lumen.

The housing 12 is then removed from the vessel and the entry site is closed using conventional sterile technique.

Thus, the device 10 of the present invention provides a combined diagnostic and therapeutic tool which can be utilized to remove obstructions in blood vessels and the like and which provides accurate and efficient means for visualizing the dimensions and configuration of a pathological growth or the like in the vessel with minimal risk of thermal injury to the vessel itself or to other surrounding normal structures. Further, the device provides a self-contained imaging system which does not require occlusion of the blood flow within the vessel to be treated when visualizing the obstructions therein. Moreover, the device of the present invention permits confirmation of reopening of the obstructed lumen without the need for repetitive injection of contrast materials or the like between therapeutic applications. Consequently, the device of the present invention provides an efficient means for reopening obstructed vascular passageways requiring a minimum length of time of intervention therein and which is capable of being constructed economically to permit disposal of the device after each use.

Although the invention has been herein shown and described in what is conceived to be the most practical and preferred embodiment, it is recognized that departures may be made therefrom within the scope of the invention which is not to be limited to the illustrative details disclosed.

Having described my invention, what I claim as new and desire to secure by Letters Patent is:

1. A device permitting imaging and removing obstructions from blood vessels and the like of a patient, the device comprising,
   a flexible housing dimensioned for insertion within a blood vessel;
   laser means borne by the housing for transmitting laser energy externally of the housing to an obstruction in said blood vessel to destroy a portion of the obstruction; and
   ultrasound means borne by the housing for generating ultrasonic waves and having a piezoelectric portion adapted to generate electric signals, upon contact by ultrasonic waves echoed from a solid object, for analysis externally of the patient to create an image of the solid object.

2. The device of claim 1 wherein the laser means and the ultrasound means are operable independently of each other.

3. The device of claim 2 wherein the ultrasound means has an electrode portion connected to said piezoelectric portion to conduct electrical energy to the piezoelectric portion to generate said ultrasonic waves.

4. A device for imaging and removing obstructions in blood vessels and the like comprising
   an elongated, substantially flexible housing dimensioned for insertion within a blood vessel and having a proximal end portion and an opposite, distal end portion, and providing a chamber communicating between the proximal end portion and distal end portion;
   a fiberoptic bundle mounted within the housing having a plurality of elongated fibers extended from the proximal end portion to the distal end portion, the fibers being disposed in predetermined spaced relation to each other, each fiber being adapted to conduct a laser beam from a source of laser energy and to transmit the beam externally of the housing to an obstruction to destroy a portion of the obstruction; and
   an ultrasound assembly borne by the housing having a piezoelectric portion and an electrode portion connected to the piezoelectric portion, the electrode portion being adapted to be connected to a source of energy to conduct electrical energy to the piezoelectric portion to cause the piezoelectric portion to generate ultrasonic waves, and the piezoelectric portion being adapted to generate electric signals upon contact thereof by ultrasonic waves echoed from a solid object, and the electrode portion being further adapted to conduct the electric signals from the piezoelectric portion to the source of energy for analysis of the signals to create an image of the solid object.

5. The device of claim 4 wherein the fiberoptic bundle mounts the piezoelectric portion.

6. The device of claim 5 wherein the piezoelectric portion includes a piezoelectric material having substantially high piezoelectric properties, and the material is coated on portions of a selected number of the fibers of the fiberoptic bundle.

7. The device of claim 6 wherein the piezoelectric material is coated on the fibers substantially over the entire length of each fiber.

8. The device of claim 6 wherein the material is coated on the fibers on portions of the fibers disposed within the proximal end portion of the housing.

9. The device of claim 8 wherein the housing mounts sound absorbing material within the chamber intermediate the distal end portion and proximal end portion in substantially occluding relation to the chamber and in substantially circumscribing relation to the fibers of the fiberoptic bundle.

10. The device of claim 9 wherein the portions of the fibers not coated with piezoelectric material are coated with material having sound absorbent properties.

11. The device of claim 10 wherein the housing mounts a lens on the distal end portion thereof adapted to focus the laser beams conducted by the fibers at a predetermined focal point.

12. The device of claim 11 wherein the housing mounts a marker externally of the distal end portion of the housing adapted to be visualized by fluoroscopy when the housing is inserted in a blood vessel.

13. The device of claim 12 wherein the housing is substantially annular in cross section and the diameter of the distal end portion of the housing is less than that of the proximal end portion.

14. The device of claim 4 wherein the housing provides an elongated tubular portion extending from the distal end portion to the proximal end portion within the chamber and providing a bore communicating externally at a first end thereof through a port defined by a portion of the distal end portion and through an exit portion communicating with the chamber in the proximal end portion of the housing to permit the flow of blood from the port to the exit portion when the housing is inserted in a blood vessel.

15. The device of claim 4 wherein the fibers of the fiberoptic bundle are each constructed of a material having high piezoelectric properties.

16. A device for imaging and removing obstructions in blood vessels and the like comprising
   an elongated, substantially flexible tubular housing having a predetermined proximal end portion, an opposite externally open distal end portion spaced a predetermined distance from the proximal end portion and dimensioned for insertion within a blood vessel, and an internal chamber extending from the proximal end portion to the distal end portion;
   a fiberoptic bundle providing a plurality of fibers mounted in the housing chamber and disposed in predetermined spaced relation to each other, each fiber providing a distal terminus disposed within the chamber in the distal end portion of the housing and an opposite, proximal terminus, the proximal termini being collected in a connector portion adapted to be connected to a source of laser energy to conduct laser beams from the source axially through the fibers to transmit the laser beams externally of the housing through the open distal end portion to destroy obstructions disposed distally thereof;
   a piezoelectric portion adapted to generate ultrasonic waves of predetermined wavelengths in a predetermined range of frequencies upon the application of electrical impulses thereto and to generate electrical impulses upon the application of ultrasonic waves thereto;

an electrode bundle mounted by the housing and connected to the piezoelectric portion, the electrode bundle providing a plurality of electrodes and being adapted to be connected to a source of electrical energy to conduct electrical impulses to the piezoelectric portion and further adapted to be connected to an analysis unit to conduct electrical impulses from the piezoelectric portion to the analysis unit for analysis thereby;

and a tubular member extending within the chamber from the proximal end portion to the distal end portion of the housing and providing an externally communicating port defined in the distal end portion and a tubular connector extending from the proximal end portion and adapted for connection to an apparatus for hemodynamic measurements when the distal end portion is inserted within a blood vessel and blood is permitted to flow through the tubular member.

17. The device of claim 16 wherein the piezoelectric portion is composed of material having a known acoustic impedance.

18. The device of claim 17 wherein the piezoelectric portion is borne by a selected number of fibers in the distal end portion of the housing, and the housing mounts a substantially sound absorbent lossy backing having an acoustic impedance substantially similar to that of the material of the piezoelectric portion.

19. The device of claim 18 wherein the fibers are spaced substantially equidistantly from adjacent fibers.

20. The device of claim 19 wherein the fibers are spaced having a maximum separation between adjacent fibers substantially equal to approximately one-half of the wavelength of the ultrasonic waves the piezoelectric portion is adapted to generate.

21. The device of claim 20 wherein the housing mounts a lens adapted to focus the laser beams at a predetermined focal point distal of the distal end portion of the housing.

22. The device of claim 21 wherein the housing mounts an external protective ring dimensioned manually to be grasped for manipulation of the device.

23. The device of claim 17 wherein the piezoelectric portion is borne by the fibers in the proximal end portion of the housing.

24. The device of claim 17 wherein the piezoelectric portion and the electrode bundle are detachably secured on the distal end portion of the housing externally thereof.

* * * * *